(12) United States Patent
Maienfisch et al.

(10) Patent No.: US 8,598,130 B2
(45) Date of Patent: Dec. 3, 2013

(54) INSECTICIDAL COMBINATIONS

(75) Inventors: Peter Maienfisch, Stein (CH); Max Angst, Basel (CH); Ottmar Franz Hueter, Stein (CH); Jorge Cisneros, Basel (CH); Paulo Aramaki, Sao Paulo SP (BR); Alfred Rindlisbacher, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 13/059,552

(22) PCT Filed: Jul. 21, 2009

(86) PCT No.: PCT/EP2009/059378
§ 371 (c)(1),
(2), (4) Date: Mar. 25, 2011

(87) PCT Pub. No.: WO2010/020510
PCT Pub. Date: Feb. 25, 2010

(65) Prior Publication Data
US 2011/0190232 A1    Aug. 4, 2011

(30) Foreign Application Priority Data
Aug. 18, 2008    (GB) .................................. 0815068.2

(51) Int. Cl.
*A61K 31/7048*    (2006.01)
*A61K 31/70*    (2006.01)
*C07H 17/08*    (2006.01)

(52) U.S. Cl.
USPC ................. 514/31; 514/28; 514/25; 536/6.5; 536/4.1

(58) Field of Classification Search
USPC ............................ 514/31, 28, 25; 536/6.5, 4.1
See application file for complete search history.

(56) References Cited

FOREIGN PATENT DOCUMENTS

| | | |
|---|---|---|
| CN | 1299593 | 6/2001 |
| CN | 1309906 | 8/2001 |
| CN | 1943353 | 4/2007 |
| CN | 101390519 | 3/2009 |
| WO | 9925188 A2 | 5/1999 |
| WO | 2008009379 A2 | 1/2008 |

OTHER PUBLICATIONS

Otsuka et al. (International Plant Protection Congress, Proceedings, 16th, Glasgow, United Kingdom, Oct. 15-18, 2007 (2007), vol. 1, 46-51) (Abstract sent).*
Lasota et al. (Acta Leidensia, (1990) vol. 59, No. 1-2, pp. 217-225) (Abstract sent).*
Sasama et al. (International Plant Protection Congress, Proceedings, 16th, Glasgow, United Kingdom, Oct. 15-18, 2007 (2007), vol. 1, 46-51).*
Lasota et al. (Acta Leidensia, (1990) vol. 59, No. 1-2, pp. 217-225).*

* cited by examiner

*Primary Examiner* — Shaojia Anna Jiang
*Assistant Examiner* — Michael C Henry
(74) *Attorney, Agent, or Firm* — Brian D. McAlhaney

(57) ABSTRACT

A method of controlling or preventing damage to a plant, which comprises applying on the plant or a surrounding area thereof a combination comprising (I) abamectin, and (II) cyflumetofen, in any desired sequence or simultaneously.

19 Claims, No Drawings

INSECTICIDAL COMBINATIONS

This application is a 371 of International Application No. PCT/EP2009/059378 filed Jul. 21, 2009, which claims priority to GB 0815068.2 filed Aug. 18, 2008, the contents of which are incorporated herein by reference.

The present invention relates to the use of a defined combination of pesticidal active ingredients, and compositions thereof, and methods for using such a combination in the control or prevention of damage to a plant.

Certain active ingredients and combinations of active ingredients for controlling pest attack are described in the literature. There is a continuing need to provide pesticidal combinations, which provide improved, for example, biological properties, for example, synergistic properties, especially for controlling pathogens and/or pests, especially in coffee, citrus, apple and vegetable crops.

It is now been found that a particular combination of active ingredients provide unexpected control or prevention of damage to a plant, when the particular combination is applied on the plant or surrounding area thereof.

Accordingly, in a first aspect the present invention provides a method of controlling or preventing damage to a plant, which comprises applying on the plant or a surrounding area thereof a combination comprising (I) abamectin, and (II) cyflumetofen, in any desired sequence or simultaneously.

In a second aspect the present invention provides a method of improving the growth of a plant by applying to the plant or a surrounding area thereof a combination, as defined in the first aspect, in any desired sequence or simultaneously.

Damage to a plant is generally caused by pests, such as insects, fungi, weeds, etc, and so the control and prevention of damage to a plant generally involves control of the pests.

The combination defined in the first aspect is suitable for control of pests selected from the class Insecta, Arachnida and/or Nematoda.

In an embodiment of any aspects of the invention, (I) and (II) are applied simultaneously.

Controlling, preventing or protecting and its inflections, within the context of the present invention, mean reducing any undesired effect, such as
  pest infestation or attack of, and
  pest damage on,
a plant, part of the plant or plant propagation material to such a level that an improvement is demonstrated.

The combination can demonstrate synergistic activity compared to activity of compounds alone.

The pesticidal combination according to the invention has very advantageous properties for protecting plants against pest attack or damage; particularly in the instance of plants, the present invention can control or prevent pest damage on a plant, plant organs and/or plant grown from the a seed.

These properties are for example the synergistically enhanced actions of the combination of the compounds (I) and (II) resulting in lower pest damage, lower rates of application, or a longer duration of action. In the instance of agriculture, the enhanced actions are found to show an improvement in the growing characteristics of a plant by, for example, higher than expected control of pest damage, greater growth characteristics of the plant, greater yield of the crop of the plant, greater stand of the plant.

The improvement in the growing (or growth) characteristics of a plant can manifest in a number of different ways, but ultimately it results in a better product of the plant. It can, for example, manifest in improving the yield and/or vigour of the plant or quality of the harvested product from the plant, which improvement may not be connected to the control of pests.

As used herein the phrase "improving the yield" of a plant relates to an increase in the yield of a product of the plant by a measurable amount over the yield of the same product of the plant produced under the same conditions, but without the application of the subject method. It is preferred that the yield be increased by at least about 0.5%, more preferred that the increase be at least about 1%, even more preferred is about 2%, and yet more preferred is about 4%, or more. Yield can be expressed in terms of an amount by weight or volume of a product of the plant on some basis. The basis can be expressed in terms of time, growing area, weight of plants produced, amount of a raw material used, or the like.

As used herein the phrase "improving the vigour" of a plant relates to an increase or improvement of the vigour rating, or the stand (the number of plants per unit of area), or the plant height, or the plant canopy, or the visual appearance (such as greener leaf colour), or the root rating, or emergence, or protein content, or increased tillering, or bigger leaf blade, or less dead basal leaves, or stronger tillers, or less fertilizer needed, or less seeds needed, or more productive tillers, or earlier flowering, or early grain maturity, or less plant verse (lodging), or increased shoot growth, or earlier germination, or any combination of these factors, or any other advantages familiar to a person skilled in the art, by a measurable or noticeable amount over the same factor of the plant produced under the same conditions, but without the application of the subject method.

When it is said that the present method is capable of "improving the yield and/or vigour" of a plant, the present method results in an increase in either the yield, as described above, or the vigor of the plant, as described above, or both the yield and the vigor of the plant.

Accordingly, the present invention also provides a method of improving the growing characteristics of a plant, which comprises applying to the plant the combination, as defined in the first aspect, in any desired sequence or simultaneously.

The combination of the invention can be used in the agricultural sector and related fields of use for controlling or preventing pest damage on plants.

Also made available herein is a composition comprising (I) abamectin and (II) cyflumetofen. In an embodiment, the composition is a pesticidal composition, such as insecticidal, arachnicidal and/or nematicidal composition.

In a preferred embodiment the combination is in the form of a composition, which composition may further comprise one or more customary formulation auxiliaries. In a preferred embodiment, the composition is in the form of a pre-mix formulated composition.

Examples of pests controlled by the combination according to the invention are pests selected from the class Insecta, Arachnida and Nematoda. Examples of such pests include:
from the order Lepidoptera, for example, *Acleris* spp., *Adoxophyes* spp., *Aegeria* spp., *Agrotis* spp., *Alabama argillaceae*, *Amylois* spp., *Anticarsia gemmatalis*, *Archips* spp., *Argyrotaenia* spp., *Autographa* spp., *Busseola fusca*, *Cadra cautella*, *Carposina nipponensis*, *Chilo* spp., *Choristoneura* spp., *Clysia ambiguella*, *Cnaphalocrocis* spp., *Cnephasia* spp., *Cochylis* spp., *Coleophora* spp., *Crocidolomia* spp., *Cryptophlebia leucotreta*, *Crysodeixis includens*, *Cydia* spp., *Diatraea* spp., *Diparopsis castanea*, *Earias* spp., *Elasmopalpus* spp., *Ephestia* spp., *Eucosma* spp., *Eupoecilia ambiguella*, *Euproctis* spp., *Euxoa* spp., *Grapholita* spp., *Hedya nubiferana*, *Heliothis* spp., *Hellula undalis*, *Hyphantria cunea*, *Keiferia lycopersicella*, *Leucoptera scitella*, *Lithocollethis* spp., *Lobesia botrana*, *Lymantria* spp., *Lyonetia* spp., *Malacosoma* spp., *Mamestra brassicae*, *Manduca sexta*, *Operophtera* spp.,

*Ostrinia nubilalis, Pammene* spp., *Pandemis* spp., *Panolis flammea, Pectinophora gossypiella, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;

from the order Coleoptera, for example, *Agriotes* spp., *Anthonomus* spp., *Atomaria linearis, Ceutorhynchus* spp., *Chaetocnema tibialis, Cosmopolites* spp., *Curculio* spp., *Dermestes* spp., *Diabrotica* spp., *Epilachna* spp., *Eremnus* spp., *Gonocephalum* spp., *Heteronychus* spp., *Leptinotarsa decemlineata, Lissorhoptrus* spp., *Melolontha* spp., *Orycaephilus* spp., *Otiorhynchus* spp., *Phlyctinus* spp., *Phyllotreta* spp., *Popillia* spp., *Protostrophus* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.;

from the order Orthoptera, for example, *Blatta* spp., *Blattella* spp., *Gryllotalpa* spp., *Leucophaea maderae, Locusta* spp., *Periplaneta* spp. and *Schistocerca* spp.;

from the order Isoptera, for example, *Reticulitermes* spp.;

from the order Psocoptera, for example, *Liposcelis* spp.;

from the order Anoplura, for example, *Haematopinus* spp., *Linognathus* spp., *Pediculus* spp., *Pemphigus* spp. and *Phylloxera* spp.;

from the order Mallophaga, for example, *Damalinea* spp. and *Trichodectes* spp.;

from the order Thysanoptera, for example, *Frankliniella* spp., *Hercinothrips* spp., *Taeniothrips* spp., *Thrips palmi, Thrips tabaci* and *Scirtothrips aurantii;* from the order Heteroptera, for example, *Dichelops melacanthus, Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Triatoma* spp.;

from the order Homoptera, for example, *Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Paratoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri;* from the order Hymenoptera, for example, *Acromyrmex, Athalia rosae, Atta* spp., *Cephus* spp., *Diprion* spp., *Diprionidae, Gilpinia polytoma, Hoplocampa* spp., *Lasius* spp., *Monomorium pharaonis, Neodiprion* spp., *Solenopsis* spp. and *Vespa* spp.;

from the order Diptera, for example, *Antherigona soccata, Bibio hortulanus, Ceratitis* spp., *Chrysomyia* spp., *Culex* spp., *Cuterebra* spp., *Dacus* spp., *Delia* spp., *Drosophila melanogaster, Liriomyza* spp., *Melanagromyza* spp., *Orseolia* spp., *Oscinella frit, Pegomyia hyoscyami, Phorbia* spp., *Rhagoletis pomonella, Sciara* spp.;

from the order Acarina, for example, *Acarus siro, Aceria sheldoni, Aculus schlechtendali, Amblyomma* spp., *Argas* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Olygonychus pratensis, Ornithodoros* spp., *Panonychus* spp., *Phyllocoptruta* spp. (such as *Phyllocoptruta oleivora*), *Polyphagotarsonemus latus, Psoroptes* spp., *Rhipicephalus* spp., *Rhizoglyphus* spp., *Sarcoptes* spp., *Tarsonemus* spp. and *Tetranychus* spp.; and from the class Nematoda, for example, the species of *Meloidogyne* spp. (for example, *Meloidogyne incoginita* and *Meloidogyne javanica*), *Heterodera* spp. (for example, *Heterodera glycines, Heterodera schachtii, Heterodora avenae* and *Heterodora trifolii*), *Globodera* spp. (for example, *Globodera rostochiensis*), *Radopholus* spp. (for example, *Radopholus similes*), *Rotylenchulus* spp., *Pratylenchus* spp. (for example, *Pratylenchus neglectans* and *Pratylenchus penetrans*), *Aphelenchoides* spp., *Helicotylenchus* spp., *Hoplolaimus* spp., *Paratrichodorus* spp., *Longidorus* spp., *Nacobbus* spp., *Subanguina* spp. *Belonlaimus* spp., *Criconemella* spp., *Criconemoides* spp. *Ditylenchus* spp., *Dolichodorus* spp., *Hemicriconemoides* spp., *Hemicycliophora* spp., *Hirschmaniella* spp., *Hypsoperine* spp., *Macroposthonia* spp., *Melinius* spp., *Punctodera* spp., *Quinisulcius* spp., *Scutellonema* spp., *Xiphinema* spp., and *Tylenchorhynchus* spp.

In particular the combination is suitable for control of one or more of *Panonychus* spp., *Brevipalpus* spp., *Tetranychus* spp. and *Phyllocoptruta* spp.

The combination of the invention can be formulated for a particular use. Preferably, each combination is formulated for protecting cultivated plants or their propagation materials. Accordingly, each combination of the invention can be applied to the plant in a conventional manner, such as foliar spray.

Further, the present invention also envisages soil application of the combination of the invention to control the soil-dwelling pests and/or soil-borne pathogens. Methods of applying to the soil can be via any suitable method, which ensures that the combination penetrates the soil, for example, nursery tray application, in furrow application, soil drenching, soil injection, drip irrigation, application through sprinklers or central pivot, incorporation into soil (broad cast or in band) are such methods.

The present invention also provides a method of controlling or preventing pest damage in a plant propagation material and a plant, part of a plant and/or plant organ that grow at a later point in time, which comprises applying on the plant propagation material or a surrounding area thereof, the ingredients of the combination as defined in the first aspect, in any desired sequence or simultaneously.

Also provided is a method of protecting a plant propagation material and a plant, part of a plant and/or plant organ that grow at a later point in time against pest damage by applying to the plant propagation material or a surrounding area thereof the ingredients of the combination, as defined in the first aspect, in any desired sequence or simultaneously.

Further, in an embodiment the present invention relates to a method which comprises (i) treating a plant propagation material, such as a seed, with a combination as defined in the first aspect, and (ii) planting or sowing the treated propagation material, wherein the combination protects against pest damage of the treated plant propagation material, or part of plant, plant organ and/or plant grown from the treated propagation material.

Also, in an embodiment the present invention relates to a method which comprises (i) treating a plant propagation material, such as a seed, with a combination as defined in the first aspect, and (ii) planting or sowing the treated propagation material, and (iii) achieving protection against pest damage of the treated plant propagation material, or part of plant, plant organ and/or plant grown from the treated propagation material.

The term "plant propagation material" is understood to denote all the generative parts of the plant, such as seeds, which can be used for the multiplication of the latter and vegetative plant materials such as cuttings and tubers (for example, potatoes). Accordingly, as used herein, part of a plant includes propagation material. There may be mentioned, e.g., the seeds (in the strict sense), roots, fruits, tubers, bulbs, rhizomes, parts of plants. Germinated plants and young plants, which are to be transplanted after germination or after emergence from the soil, may also be mentioned. These young plants may be protected before transplantation by a total or partial treatment by immersion.

Parts of plant and plant organs that grow at later point in time are any sections of a plant that develop from a plant propagation material, such as a seed. Parts of plant, plant organs, and plants can also benefit from the pest damage protection achieved by the application of each combination on to the plant propagation material. In an embodiment, certain parts of a plant and certain plant organs that grow at later point in time can also be considered as plant propagation material, which can themselves be applied (or treated) with the combination; and consequently, the plant, further parts of the plant and further plant organs that develop from the treated parts of plant and treated plant organs can also benefit from the pest damage protection achieved by the application of the combination on to the certain parts of plant and certain plant organs.

Methods for applying or treating pesticidal active ingredients and mixtures thereof on to plant propagation material, especially seeds, are known in the art, and include dressing, coating, pelleting and soaking application methods of the propagation material. Such methods are also applicable to the combination according to the invention. In a preferred embodiment, the combination is applied or treated on to the plant propagation material by a method such that the germination is not induced; generally seed soaking induces germination because the moisture content of the resulting seed is too high. Accordingly, examples of suitable methods for applying (or treating) a plant propagation material, such as a seed, is seed dressing, seed coating or seed pelleting and alike.

It is preferred that the plant propagation material is a seed.

Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed may also be primed either before or after the treatment.

Even distribution of the ingredients in the combination and adherence thereof to the seeds is desired during propagation material treatment. Treatment could vary from a thin film (dressing) of the formulation containing the combination, for example, a mixture of active ingredient(s), on a plant propagation material, such as a seed, where the original size and/or shape are recognizable to an intermediary state (such as a coating) and then to a thicker film (such as pelleting with many layers of different materials (such as carriers, for example, clays; different formulations, such as of other active ingredients; polymers; and colourants) where the original shape and/or size of the seed is no longer recognisable.

An aspect of the present invention includes application of the combination onto the plant propagation material in a targeted fashion, including positioning the ingredients in the combination onto the entire plant propagation material or on only parts thereof, including on only a single side or a portion of a single side. One of ordinary skill in the art would understand these application methods from the description provided in EP954213B1 and WO06112700.

The combination described herein can also be used to enhance the growth of a plant through treating, or applying, a combination according to the present on to a "pill" or a suitable substrate and placing, or sowing, the treated pill, or substrate, next to a plant propagation material. Such techniques are known in the art, particularly in EP1124414, WO07067042, and WO07067044.

Application of the combination described herein onto plant propagation material also includes protecting the plant propagation material treated with the combination of the present invention by placing one or more pesticide-containing particles next to a pesticide-treated seed, wherein the amount of pesticide is such that the pesticide-treated seed and the pesticide-containing particles together contain an Effective Dose of the pesticide and the pesticide dose contained in the pesticide-treated seed is less than or equal to the Maximal Non-Phytotoxic Dose of the pesticide. Such techniques are known in the art, particularly in WO2005/120226.

Application of the combination onto the seed also includes controlled release coatings on the seeds, wherein the ingredients of the combination are incorporated into materials that release the ingredients over time. Examples of controlled release seed treatment technologies are generally known in the art and include polymer films, waxes, or other seed coatings, wherein the ingredients may be incorporated into the controlled release material or applied between layers of materials, or both.

Seed can be treated by applying thereto the compounds (I) and (II) in any desired sequence or simultaneously.

The seed treatment occurs to an unsown seed, and the term "unsown seed" is meant to include seed at any period between the harvest of the seed and the sowing of the seed in the ground for the purpose of germination and growth of the plant.

Treatment to an unsown seed is not meant to include those practices in which the active ingredient is applied to the soil but would include any application practice that would target the seed during the planting process.

Preferably, the treatment occurs before sowing of the seed so that the sown seed has been pre-treated with the combination. In particular, seed coating or seed pelleting are preferred in the treatment of the combination according to the invention. As a result of the treatment, the ingredients in each combination are adhered on to the seed and therefore available for pest control.

The treated seeds can be stored, handled, sowed and tilled in the same manner as any other active ingredient treated seed.

The combination according to the present invention is suitable for plants of the crops: cereals, such as wheat, barley, rye, oats, rice, maize (fodder maize and sugar maize/sweet and field corn) or sorghum; beet, such as sugar or fodder beet; fruit, for example pomaceous fruit, stone fruit, tree nut or soft fruit, such as apples, pears, plums, peaches, bananas, almonds, walnuts, pistachios, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, marrow, cucumbers or melons; fibre plants, such as cotton, flax, hemp or jute; citrus fruit, such as oranges, lemons, grapefruit or tangerines; vegetables, such as spinach, lettuce, asparagus, cabbages, iceberg, carrots, onions, tomatoes, paprika, potatoes or bell peppers; Lauraceae, such as avocado, Cinnamonium or camphor; and also tobacco, nuts, coffee, eggplants, sugarcane, tea, pepper, grapevines, hops, the plantain family, latex plants, lawn, turf, fodder grass, and ornamentals roses, chrysanthemums, carnation, gerberas, petunias, geranium/pelargoniums, pansies and impatiens; and shrubs, broad-leaved trees and evergreens, such as conifers. In particular, the combination is suitable for coffee, citrus, stone fruits (especially apple, pears, plums, peaches), tree nuts (especially almonds and pistachios), and vegetable crops.

Suitable target crops also include transgenic crop plants of the foregoing types. The transgenic crop plants used according to the invention are plants, or propagation material thereof, which are transformed by means of recombinant DNA technology in such a way that they are—for instance—capable of synthesizing selectively acting toxins as are known, for example, from toxin-producing invertebrates, especially of the phylum Arthropoda, as can be obtained from *Bacillus thuringiensis* strains; or as are known from plants, such as lectins; or in the alternative capable of expressing a herbicidal or fungicidal resistance. Examples of such toxins, or transgenic plants which are capable of synthesizing such toxins, have been disclosed, for example, in EP-A-0 374 753, WO 93/07278, WO 95/34656, EP-A-0 427 529 and EP-A-451 878 and are incorporated by reference in the present application.

The combination according to the present invention is particularly well suited for combating

| Pest | Crop |
|---|---|
| *Panonychus* spp. | citrus, pome fruits, stone fruits, tree nuts |
| *Brevipalpus* spp. | citrus, coffee |
| *Phyllocoptruta* spp.. | citrus |
| *Tetranychus* spp. | all of the above and vegetables |

The weight ratio of active ingredient compounds in each combination is selected as to give the desired, for example, synergistic action. In an embodiment, the weight ratio of (I) to (II) is from 100:1 to 1:100, preferably 50:1 to 1:50, more preferably 1:1 to 1:50, especially 1:5 to 1:40, advantageously 1:7 to 1:40, such as 1:10 to 1:30.

The rates of application (use) of the combination vary, for example, according to type of use, type of crop, but is such that the active ingredients in the combination is an effective amount to provide the desired enhanced action (such as pest control) and can be determined by trials and routine experimentation known to one of ordinary skill in the art. Generally for foliar or soil treatments, application rates can vary from 0.05 to 3, preferably 0.1 to 1, kg per hectare (g/ha), of active ingredients (I) and (II).

In an embodiment, independent of other embodiments, (I) and (II) are applied at a rate of 0.1 to 75 g ai/ha and 50 to 1000 g ai/ha respectively, such as 0.1 to 50 g ai/ha of (I) and 75 to 900 g ai/ha of (II); in a preferred embodiment (I) and (II) are applied at a rate of 1 to 45 g ai/ha and 100 to 800 g ai/ha respectively, especially 2 to 40 g ai/ha and 125 to 700 g ai/ha respectively.

A single pesticidal active ingredient may have activity in more than one area of pest control, for example, a pesticide may have fungicide, insecticide and nematicide activity. Specifically, aldicarb is known for insecticide, acaricide and nematicide activity, while metam is known for insecticide, herbicide, fungicide and nematicide activity, and thiabendazole and captan can provide nematicide and fungicide activity.

The combination of the present invention may be mixed or used with one or more other pesticides, such as other fungicides, insecticides, herbicides and nematicides, and/or one or more adjuvants (a substance which in itself doesn't show pesticidal activity but enhances the activity of the pesticide—usually crop oil concentrates and surfactants)

In the event one or more other pesticides are used in combination with the combination defined in the first aspect. The one or more other pesticides can be also applied to the plant, plant propagation material, or surrounding area thereof, wherein each other pesticide can be applied, independently of each other, prior to, simultaneously, or after the application of (I) and (II), and in the instance (I) and (II) are applied separately, each other pesticide can be applied, independently of each other, prior to, simultaneously, between or after the application of (I) and (II).

In an embodiment, the combination of the present invention further comprises one or more other pesticides; therefore, a composition comprises (I), (II) and one or more other pesticides.

The compounds of the combination (i.e. (I), and (II)), and any other pesticides, may be used either in pure form, i.e., as a solid active ingredient, for example, in a specific particle size, or preferably together with at least one of the auxiliary (also known as adjuvants) customary in formulation technology, such as extenders, e.g., solvents or solid carriers, or surface-active compounds (surfactants), in the form of a formulation, in the present invention. Generally, the compounds (I), and (II) are each in the form of a formulation composition with one or more of customary formulation auxiliaries.

Therefore, (I) and (II) can be used in the form of separate formulations. The compounds can be applied to the locus where control is desired either simultaneously or in succession at short interval, for example on the same day, if desired together with further carriers, surfactants or other application-promoting adjuvants customarily employed in formulation technology. In a preferred embodiment, (I) and (II) are applied simultaneously.

In the event compounds of the combination (i.e. (I), and (II)) are applied simultaneously in the present invention, they may be applied as a composition containing the combination, in which case each of (I), and (II) can be obtained from a separate formulation source and mixed together (known as a tank-mix, ready-to-apply, spray broth, or slurry), optionally with other pesticides, or (I), and (II) can be obtained as single formulation mixture source (known as a pre-mix, concentrate, formulated product), and optionally mixed together with other pesticides.

In an embodiment, the combination of the present invention is applied as a composition.

Accordingly, the present invention includes a composition comprising, as active ingredients, (I), and (II), and optionally other pesticides, and optionally one or more customary formulation auxiliaries; which may be in the form of a tank-mix or pre-mix composition.

In an embodiment, the combination of (I), and (II) is provided in the form of a pre-mix composition (or formulated product).

Alternative to the actual synergistic action with respect to pesticidal activity, the combination according to the invention also can have surprising advantageous properties which can also be described, in a wider sense, as synergistic activity.

Examples of such advantageous properties that may be mentioned are: advantageous behaviour during formulation and/or upon application, for example upon grinding, sieving, emulsifying, dissolving or dispensing; increased storage stability; improved stability to light; more advantageous degradability; improved toxicological and/or ecotoxicological behaviour; or any other advantages familiar to a person skilled in the art.

Examples of foliar formulation types for pre-mix compositions are:
GR: Granules
WP: wettable powders
WG: water dispersable granules (powders)
SG: water soluble granules
SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion.

Examples of formulation types suitable for tank-mix compositions are solutions, dilute emulsions, suspensions, or a mixture thereof, and dusts.

As with the nature of the formulations, the methods of application, such as foliar, drench, spraying, atomizing, dusting, scattering, coating or pouring, are chosen in accordance with the intended objectives and the prevailing circumstances.

The tank-mix compositions are generally prepared by diluting with a solvent (for example, water) the one or more pre-mix compositions containing different pesticides, and optionally further auxiliaries, including adjuvants.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilizers.

The formulations are prepared in known manner, e.g., by homogeneously mixing and/or grinding the active ingredients with extenders, e.g., solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g., for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable nonsorbent carriers are, for example, calcite or sand. In addition, a great number of pregranulated materials of inorganic or organic nature can be used, e.g., especially dolomite or pulverized plant residues.

Depending upon the nature of the active ingredient compounds to be formulated, suitable surface-active compounds are non-ionic, cationic and/or anionic surfactants having good emulsifying, dispersing and wetting properties. The term "surfactants" will also be understood as comprising mixtures of surfactants.

Particularly advantageous application-promoting adjuvants are also natural or synthetic phospholipids of the cephalin and lecithin series, e.g., phosphatidylethanolamine, phosphatidylserine, phosphatidylglycerol and lysolecithin.

Generally, a tank-mix formulation for foliar or soil application comprises 0.1 to 20%, especially 0.1 to 15%, active ingredient compounds, and 99.9 to 80%, especially 99.9 to 85%, of a solid or liquid auxiliaries (including, for example, a solvent such as water), where the auxiliaries can be a surfactant in an amount of 0 to 20%, especially 0.1 to 15%, based on the tank-mix formulation.

Typically, a pre-mix formulation for foliar application comprises 0.1 to 99.9%, especially 1 to 95%, active ingredient compounds, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

In general, the pre-mix compositions of the invention contain 0.5 to 99.9 especially 1 to 95, advantageously 1 to 50, %, by mass of the desired ingredients, and 99.5 to 0.1, especially 99 to 5, %, by mass of a solid or liquid adjuvant (including, for example, a solvent such as water), where the auxiliaries (or adjuvant) can be a surfactant in an amount of 0 to 50, especially 0.5 to 40, %, by mass based on the mass of the pre-mix formulation.

Whereas commercial products will preferably be formulated as concentrates (e.g., pre-mix composition (formulation)), the end user will normally employ dilute formulations (e.g., tank mix composition).

Preferred pre-mix formulations of (I) and (II) together are aqueous suspension concentrates, emulsifiable concentrates and emulsion in water.

In an preferred embodiment, the combination of the invention is in the form of a formulated pre-mix composition, and in such an instance can therefore also be used in combination with other pesticides and pesticidal formulations, formulation auxiliaries, and adjuvants (a substance which in itself doesn't show pesticidal activity but enhances the activity of the pesticide—usually crop oil concentrates and surfactants).

It is typical that the formulated pre-mix composition is used in combination with other components (for example, those mentioned above) in a tank-mix and applied to the field and/or plant.

Examples of adjuvants include branded products Penetrator, Adigor, Agora, Atplus 411F, and also oil In general, the pre-mix compositions of the invention contain 0.5 to 99.9 especially 1 to 95, advantageously 1 to 50, %, by mass of active ingredient compounds, and 99.5 to 0.1, especially 99 to 5, %, by mass of a solid or liquid adjuvant (including, for example, a solvent such as water), where the auxiliaries (or adjuvant) can be a surfactant in an amount of 0 to 50, especially 0.5 to 40, %, by mass based on the mass of the pre-mix formulation.

In a preferred embodiment, the combination is in the form of a formulated pre-mix composition comprising (I) abamectin and (II) cyflumetofen, and one or more customary formulation auxiliaries.

The Examples which follow serve to illustrate the invention.

FORMULATION EXAMPLES

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The active ingredient is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination, or of each of these compounds from (I), and (II) separately, are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Using such formulations, either straight or diluted, plant can be treated and protected against damage, for example, from pest(s), by, for example, spraying, or pouring.

The active ingredient combination according to the invention is distinguished by the fact that they are especially well tolerated by plants and are environmentally friendly.

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

Use of a term in a singular form also encompasses that term in plural form and vice a versa.

Abamectin and cyflumetofen are active ingredients for use in the agrochemical industry (also known as pesticides). Cyflumetofen is represented by the structure below and originates from Otsuka company.

A description of the other pesticides (e.g., fungicides, insecticides, nematicides) can be found in the e-Pesticide Manual, version 3.1, 13th Edition, Ed. CDC Tomlin, British Crop Protection Council, 2004-05.

The following Examples are given by way of illustration and not by way of limitation of the invention.

EXAMPLES

An unexpected effect exists whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

ppm=milligrams of active ingredient (=a.i.) per liter of spray mixture

X=% action by active ingredient A) using p ppm of active ingredient

Y=% action by active ingredient B) using q ppm of active ingredient.

According to COLBY, the expected (additive) action of active ingredients A)+B) using p+q ppm of active ingredient is $$E = X + Y - \frac{X \cdot Y}{100}$$

If the action actually observed (O is greater than the expected action (E), then the action of the combination is super-additive, i.e. there is a synergistic effect.

Trials are conducted on field beans variety Paloma to determine the effects of the present combination.

The trials are carried out on a plot is 1 m², with three replicates for each trial and spray volume ranges from 1500-1600 l/ha.

The solo and the combination products are applied three times at the rates indicated in the table below. The first application of the pesticide formulation (whether solo or combination) is at pest threshold as foliar spray (at 35 days after planting). Thereafter the second and third foliar applications are at 42 and 49 days after planting.

The assessment of the mite control is carried out on the basis of number of mites on five leaves for each plot at the times indicated in the table (i.e., six days after application 1 (6DAA1), six days after application 2 (6DAA2), 6 days after application 3 (6DAA3), and fourteen days after application 3 (14DAA3)). The values are given as a percentage compared to a non-treated control.

The Table below also provides the expected % control for the combination based on the Colby formula.

| | Rate | Observed, % control of mites | | | | Expected, % control of mites | | | |
|---|---|---|---|---|---|---|---|---|---|
| | g/ha | 6DAA1 | 6DAA2 | 6DAA3 | 14DAA3 | 6DAA1 | 6DAA2 | 6DAA3 | 14DAA3 |
| Abamectin | 6.7 | 92 | 32 | 59 | 66 | — | — | — | — |
| cyflumetofen | 150 | 79 | 64 | 26 | 32 | — | — | — | — |
| combination | 6.7 & 150 | 100 | 80 | 92 | 94 | 98 | 76 | 70 | 77 |

The invention claimed is:

1. A method of controlling or preventing damage to a plant, which comprises applying on the plant, or a surrounding area thereof, a combination comprising synergistically effective amounts of (I) abamectin and (II) cyflumetofen, in any desired sequence or simultaneously, wherein the weight ratio of (I) to (II) is from 1:7 to 1:40.

2. A method of improving the growth of a plant by applying to the plant, or a surrounding area thereof, a combination, as defined in claim 1, in any desired sequence or simultaneously.

3. The method of claim 1 wherein damage is controlled or prevented by controlling or preventing attack on the plant by a pest selected from the class Insecta, Arachnida and Nematoda.

4. The method according to claim 1 wherein (I) and (II) are applied at a rate of 1.25 to 75 g ai/ha and 50 to 1000 g ai/ha respectively.

5. The method according to claim 1 wherein (I) and (II) are applied simultaneously.

6. The method according to claim 1 wherein one or more other pesticides are also applied to the plant, or surrounding area thereof, wherein each other pesticide can be applied, independently of each other, prior to, simultaneously, or after the application of (I) and (II), and in the instance (I) and (II) are applied separately, each other pesticide can be applied, independently of each other, prior to, simultaneously, between or after the application of (I) and (II).

7. The method according to claim 1 wherein abamectin and cyflumetofen are each in a form of a formulated composition.

8. The method according to claim 1 wherein (I) and (II) are together in the form of a single formulated composition, wherein the single formulated composition further comprises one or more formulation auxiliaries.

9. A method of protecting (a) plant propagation material and (b)(i) a plant, (ii) a part of a plant, or (iii) a plant organ that grows from the plant propagation material against pest damage, said method comprising applying to the plant propagation material a combination comprising synergistically effective amounts of (I) abamectin and (II) cyflumetofen, in any desired sequence or simultaneously, to form treated plant propagation material, wherein the weight ratio of (I) to (II) is from 1:7 to 1:40.

10. A composition comprising synergistically effective amounts of (I) abamectin and (II) cyflumetofen, wherein the weight ratio of (I) to (II) is from 1:7 to 1:40.

11. A composition comprising synergistically effective amounts of (I) abamectin and (II) cyflumetofen, and one or more formulation auxiliaries, wherein the weight ratio of (I) to (II) is from 1:7 to 1:40.

12. A formulated pre-mix composition comprising synergistically effective amounts of (I) abamectin and (II) cyflumetofen, and one or more formulation auxiliaries, wherein the weight ratio of (I) to (II) is from 1:7 to 1:40.

13. The method of claim 1, further comprising planting or sowing the treated plant propagation material.

14. The method of claim 4, wherein (I) and (II) are applied at a rate of 3.125 to 40 g ai/ha and 125 to 700 g ai/ha respectively.

15. The method of claim 9, wherein (I) and (II) are applied at a rate of 1.25 to 75 g ai/ha and 50 to 1000 g ai/ha respectively.

16. The method of claim 15, wherein (I) and (II) are applied at a rate of 3.125 to 40 g ai/ha and 125 to 700 g ai/ha respectively.

17. The composition of claim 10, wherein (I) and (II) are present in an amount of 1.25 to 75 g ai/ha and 50 to 1000 g ai/ha respectively.

18. The composition of claim 17, wherein (I) and (II) are present in an amount of 3.125 to 40 g ai/ha and 125 to 700 g ai/ha respectively.

19. The formulated pre-mix composition of claim 12, wherein (I) and (II) are present in an amount of 3.125 to 40 g ai/ha and 125 to 700 g ai/ha respectively.

* * * * *